(12) United States Patent
Bertran et al.

(10) Patent No.: US 9,505,771 B2
(45) Date of Patent: Nov. 29, 2016

(54) STABLE MICRONISED MONOCLIN FORM OF ASENAPINE MALEATE AND ITS SYNTHESIS

(75) Inventors: Agusti Bertran, Barcelona (ES); Josep Terradas, Barcelona (ES)

(73) Assignee: Laboratories Lesvi S.L., Barcelona (ES)

( * ) Notice: Subject to any disclaimer, the term of this patent is extended or adjusted under 35 U.S.C. 154(b) by 69 days.

(21) Appl. No.: 14/118,476

(22) PCT Filed: May 18, 2012

(86) PCT No.: PCT/GB2012/000450
§ 371 (c)(1),
(2), (4) Date: Jan. 21, 2014

(87) PCT Pub. No.: WO2012/156677
PCT Pub. Date: Nov. 22, 2012

(65) Prior Publication Data
US 2014/0142158 A1    May 22, 2014

Related U.S. Application Data

(60) Provisional application No. 61/487,495, filed on May 18, 2011.

(51) Int. Cl.
*C07D 491/044* (2006.01)
*C07C 57/145* (2006.01)
*C07D 491/04* (2006.01)

(52) U.S. Cl.
CPC ........ *C07D 491/044* (2013.01); *C07C 57/145* (2013.01); *C07D 491/04* (2013.01)

(58) Field of Classification Search
CPC ............ C07D 491/044; C07D 491/04; A61K 31/407; C07B 2200/13; C07B 57/145; Y10T 428/2982; C07C 57/145
See application file for complete search history.

(56) References Cited

U.S. PATENT DOCUMENTS

| 5,763,476 | A * | 6/1998 | Delbressine et al. ......... 514/410 |
| 7,704,525 | B2 * | 4/2010 | Del Curto .............. A61K 9/145 |
| | | | 424/450 |
| 8,779,161 | B2 * | 7/2014 | Katkam ............. C07D 491/044 |
| | | | 548/421 |
| 8,933,114 | B2 * | 1/2015 | Ventimiglia ....... C07D 491/044 |
| | | | 514/410 |
| 2006/0229352 | A1 | 10/2006 | Kemperman et al. |
| 2007/0027134 | A1 * | 2/2007 | Heeres ..................... 514/211.12 |
| 2008/0009619 | A1 | 1/2008 | Kemperman et al. |
| 2008/0306133 | A1 * | 12/2008 | van der Sterren ... A61K 9/0043 |
| | | | 514/412 |
| 2013/0211099 | A1 * | 8/2013 | Katkam ............... C07D 491/04 |
| | | | 548/421 |
| 2013/0225835 | A1 * | 8/2013 | Dalmases Barjoan et al. ............................ 548/421 |
| 2013/0267574 | A1 * | 10/2013 | Ventimiglia ....... C07D 491/044 |
| | | | 514/410 |
| 2014/0051741 | A1 * | 2/2014 | Frigoli et al. .................. 514/410 |

FOREIGN PATENT DOCUMENTS

| EP | 1710245 A1 | 11/2006 | |
| EP | 1710245 B1 * | 8/2007 | .......... C07D 491/04 |
| EP | 1917267 B1 * | 12/2008 | .......... C07D 491/04 |
| WO | 2006106135 A1 | 10/2006 | |
| WO | 2011159903 A2 | 12/2011 | |
| WO | 2012038975 A2 | 3/2012 | |
| WO | 2012066565 A2 | 5/2012 | |
| WO | WO 2012156676 A1 * | 11/2012 | .......... C07D 491/04 |

OTHER PUBLICATIONS

"Storage Conditions for the monoclinic crystal form of the salt of a dibenzooxepinopyrrole compound with maleic acid", IP.com journal, May 17, 2012.
Funke et al., "Physico-chemical properties and stability of trans-5-chloro-2-methyl-2,3,4a,12b-tetrahydro-1H-dibenz-2;3:6,7 oxepino-4,5-c, pyrrodidine maleate", Arzeneimittel Forschung. Drug Research, vol. 40, No. 5, 1990, pp. 536-539.

* cited by examiner

*Primary Examiner* — Robert A Wax
*Assistant Examiner* — Olga V Tcherkasskaya
(74) *Attorney, Agent, or Firm* — Stites & Harbison, PLLC; Terry L. Wright

(57) ABSTRACT

A stable micronized monoclinic form of asenapine maleate is described, which comprises 5% by weight or less of orthorhombic form or any other crystalline form of asenapine maleate, wherein the asenapine maleate has a particle size distribution characterized by a d90 equal to or below 40 µm. Processes for preparing the stable micronized monoclinic form of asenapine maleate are also described. Formula (I).

10 Claims, 1 Drawing Sheet

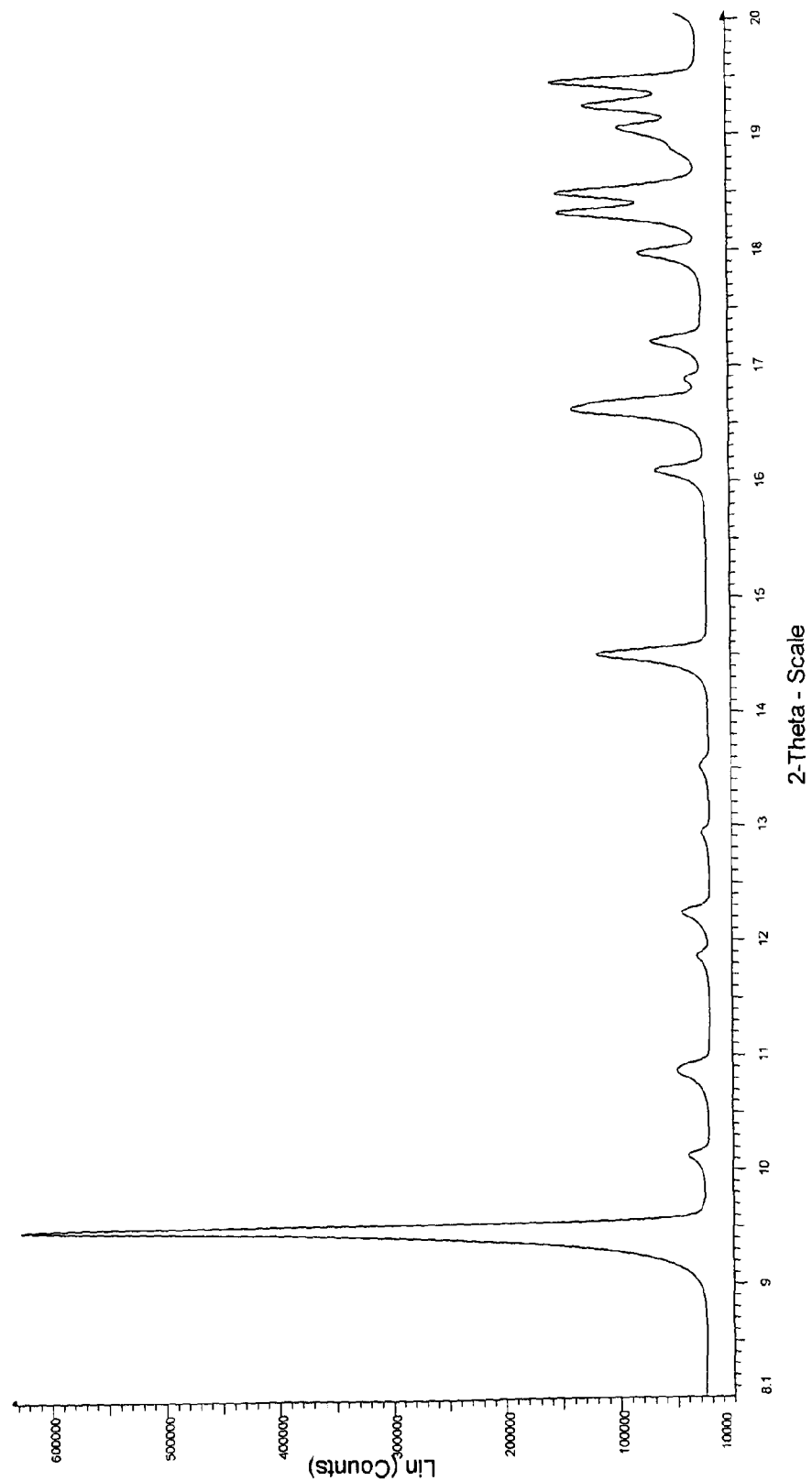

STABLE MICRONISED MONOCLIN FORM OF ASENAPINE MALEATE AND ITS SYNTHESIS

FIELD OF THE INVENTION

The present invention relates to a polymorphic form of a compound. In particular, it relates to a novel stable micronised monoclinic form of asenapine maleate, to the process for its preparation and to pharmaceutical compositions containing said stable micronised crystalline form.

BACKGROUND OF THE INVENTION

Asenapine or trans-5-chloro-2-methyl-2,3,3a,12b-tetrahydro-1H-dibenz[2,3:6,7]oxepino[4,5-c]pyrrole, was first described in U.S. Pat. No. 4,145,434 by van der Burg and is represented by a structure of Formula 1:

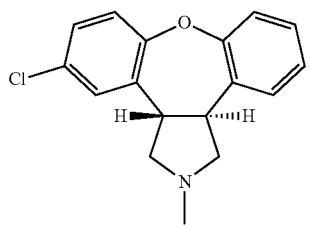

1

Asenapine is a broad-spectrum, high potency serotonin, noradrenaline and dopamine antagonist, which exhibits potential antipsychotic activity. Asenapine is marketed as its maleate salt for the treatment of schizophrenia and manic episodes associated with bipolar I disorders, in the form of sublingual tablets sold under the trademark SAPHRIS®.

Pharmaceutical compositions comprising asenapine maleate for sublingual or buccal administration were first described in EP 0 746 317 B1. These sublingual tablets were prepared by a freeze-drying (lyophilisation) process. This process involves freezing off an aqueous-based drug solution followed by sublimation of the ice in a vacuum, an undesirable process for industrial scale applications.

As described in Funke et al., Arzneim.-Forsch./Drug Res., 40:536-539 (1990), asenapine maleate (Form H) was the first known polymorphic form. Form H is a monoclinic crystalline form having a melting point in the range of 141° C. to 145° C. EP 1 710 245 B1 and EP 1 917 267 B1 described the discovery of a new form of asenapine maleate (Form L), which is an orthorhombic crystalline form having a melting point in the range of 138° C. to 142° C. EP 1 710 245 B1 and EP 1 917 267 B1 mention the importance of the particle size of asenapine maleate, since asenapine maleate is commercialised as sublingual tablets, which are dissolved in the mouth. Thus, asenapine maleate having a particle size distribution characterised by a d95 of about 100 µm or less, more preferably about 50 µm or less, and most preferably about 30 µm or less is desirable for sublingual formulations. According to EP 1 710 245 B1 and EP 1 917 267 B1, the outcome of the micronisation process used therein, and which is necessary to reduce the particle size of the asenapine maleate crystals, appeared to be unpredictable when crystals of the monoclinic form of asenapine maleate were subjected to micronisation. Crystals of the orthorhombic form were found to be present in addition to the known monoclinic form of the starting material. The present inventors have also observed that micronisation of the monoclinic crystalline form of asenapine maleate, prepared as disclosed in U.S. Pat. No. 4,145,434, resulted in mixtures of both crystalline forms (i.e. monoclinic and orthorhombic forms of asenapine maleate), which eventually evolved to the orthorhombic crystalline form. This phenomenon does not seem to occur when the orthorhombic form of asenapine maleate is micronised, as described in EP 1 710 245 B1 and EP 1 917 267. However, use of the orthorhombic form in industry is unfeasible since its preparation process comprises very long crystallization steps (between 42-72 hours), as described in EP 1 710 245 B1 and EP 1917 267 B1. As a result, the preparation of micronised orthorhombic crystalline form of asenapine maleate is an undesirable process for industrial scale applications. More favourably, the preparation of the monoclinic form of asenapine maleate involves a crystallization process which only takes about 3 hours.

In accordance with regulatory requirements of the U.S. and other countries, e.g. the FDA's Good Manufacturing Practice ("GMP") requirements, when preparing pharmaceutical compositions containing active ingredients for administration to mammals, there is a need to produce crystalline forms, or polymorphs, which are as pure and as stable as possible. Differences in the chemical and physical properties of polymorphic forms of active ingredients, such as melting point, chemical reactivity, handling properties and apparent solubility can have a direct effect on the ability to process and/or manufacture an active ingredient and its pharmaceutical compositions, as well as on its stability, dissolution rate and the bioavailability of commercial compositions. As a result, a process that provides unstable polymorphic forms is not desirable.

Therefore, it is highly desirable to develop a process which allows the reduction in size of the monoclinic form of asenapine maleate, such that it is suitable for the preparation of sublingual pharmaceutical compositions, yet following which the polymorphic stability of the asenapine maleate is maintained over time.

BRIEF DESCRIPTION OF THE INVENTION

The present invention relates to a stable micronized form of monoclinic asenapine maleate.

A second aspect of the invention provides a process for the preparation of a stable micronized monoclinic form of asenapine maleate, the process comprising the micronisation of the monoclinic form of asenapine maleate under specific conditions of temperature and pressure.

A third aspect of the invention relates to the use of the stable micronized form of monoclinic asenapine maleate for the treatment of mental disorders.

A fourth aspect of the invention relates to processes for obtaining asenapine maleate monoclinic form of high polymorphic purity, by crystallization of asenapine maleate, optionally in the presence of a surfactant.

BRIEF DESCRIPTION OF THE FIGURE

FIG. 1 shows a powder X-ray diffractogram of the monoclinic form of asenapine maleate obtained by way of Example 1.

DEFINITIONS

The term 'micronisation' as used herein refers to the process of reducing the average diameter of a solid material's particles. Usually, the term micronisation is used when the particles that are produced are only a few micrometers in diameter. Traditional micronisation techniques are based on the use of friction to reduce particle size. Such methods include milling and grinding. Reduction in particle size may also take place as a result of collision and impact.

The term 'dx' as used herein means that x % of the particles in a composition (based on volume) have a diameter of or below a specified d value. Thus, a d90 of 100 μm means that 90% of the particles, by volume, have a diameter of or below 100 μm. As well as using d90 as a measuring reference to determine particle size, d95 is occasionally used for such a purpose. Therefore, a d95 of 100 μm means that 95% of the particles, by volume, have a diameter of or below 100 μm.

The term 'micronised' as used herein when referring to the stable monoclinic form of asenapine maleate of the invention refers to a monoclinic form of asenapine maleate which has a particle size distribution characterised by a d90 equal to or below 40 μm (e.g. below 40 μm), preferably equal to or below 30 μm (e.g. below 30 μm).

The term 'jet mill' as used herein denotes a mill in which particle size is reduced by high particle acceleration produced by the expansion of micronisation gas, leading to friction, collision and impact between the particles.

The term "container" as used herein refers to an article which is used to contain, handle, store, and/or transport the stable monoclinic form of asenapine maleate of the invention. The container may be in direct contact with the asenapine maleate or a pharmaceutical composition containing the asenapine maleate. The container is so designed that the contents may be removed in a manner appropriate to the intended use of the contained asenapine maleate or pharmaceutical composition. The material used for the containers described in the context of the present invention, and used in the Examples thereof, may be any transparent or opaque material, which does not interact physically or chemically with the contents in a way that alters the quality of the asenapine maleate or pharmaceutical composition beyond the limits tolerated by official (e.g. USP and European Pharmacopeia) requirements. The contents of the container may be under ambient environmental conditions of pressure or subjected to vacuum (i.e. sub-atmospheric pressure) conditions.

DETAILED DESCRIPTION OF THE INVENTION

The present inventors have devised specific micronisation conditions that, surprisingly, allowed a novel and polymorphically stable monoclinic form of asenapine maleate to be obtained, which showed high stability, polymorphic purity and appropriate physico-mechanical properties for its manipulation at industrial scale.

The new stable monoclinic form of asenapine maleate is characterised by having a very low particle size, and a particle size distribution characterised by a d90 equal to or below 40 μm (e.g. below 40 μm), preferably equal to or below 30 μm (e.g. below 30 μm), more preferably equal to or below 10 μm (e.g. below 10 μm), which allows its use in the preparation of sublingual pharmaceutical compositions. The particle size distribution was determined by laser diffraction spectrometry (LDS). In preferred embodiments, the asenapine maleate of the invention has a particle size distribution characterised by a d95 equal to or below 40 μm (e.g. below 40 μm), preferably equal to or below 30 μm (e.g. below 30 μm), and more preferably equal to or below 10 μm (e.g. below 10 μm).

The new stable monoclinic form of asenapine maleate of the present invention, obtained by using specific micronisation conditions, is also characterised by having high polymorphic purity and stability over time, not evolving to another polymorphic form. The obtained polymorphically pure form of monoclinic asenapine maleate shows high polymorphic stability, preferably such that, after 1 month of storage, preferably after 2 months, and more preferably after 3 months, it has more than 95% by weight of the monoclinic form (to be denoted herein as 'polymorphically stable'). During the storage period of 1 month, 2 months or 3 months, a temperature of 25° C. and a relative humidity of 60%, or a temperature of 40° C. and a relative humidity of 75%, may be used. For such tests, the samples may be placed into either or both of transparent and opaque vacuum containers. In a preferred embodiment, more than 98% by weight of monoclinic form is present. Most preferably more than 99% by weight of the monoclinic form is present. Thus, the new stable monoclinic form of asenapine maleate of the invention contains 5% by weight or less of any other crystalline form, preferably less than 2% by weight of any other crystalline form, most preferably less than 1% by weight of any other crystalline form. The monoclinic and orthorhombic forms of asenapine maleate were characterised, and thus distinguished, by the powder X-ray diffraction pattern (PXRD) of the asenapine maleate, as described in EP 1710245. Characterisation of the micronised monoclinic form of asenapine maleate was carried out, and demonstrates that no significant variation in polymorphic purity occurs over time, as seen in Table 1.

Stability tests demonstrated that a micronisation process carried out at low temperature and low pressure yielded polymorphically pure monoclinic crystals of asenapine maleate of low particle size, wherein no other polymorphic forms were detected. The material remained polymorphically stable after 3 months. The same results were obtained using transparent and opaque vacuum containers. It has been also proved that material remained polymorphically stable, being more than 95% by weight of the monoclinic form, after 6 months and 12 months. The long term stability properties in different storage conditions of the stable micronized form of monoclinic asenapine maleate of the invention are of significant advantage for industrial scale applications.

A second aspect of the invention provides a process for the preparation of a new stable micronized monoclinic form of asenapine maleate, the process comprising the micronisation of monoclinic crystals of asenapine maleate under specific conditions. The specific conditions of the micronisation process of the invention concern pressure and temperature. The micronisation pressure used in the process of the present invention is below 7 bar, preferably 5 bar or below and more preferably 3 bar or below. The micronisation temperature used in the process of the present invention is equal to or below 10° C., preferably 0° C. or below and more preferably −10° C. or below.

The asenapine maleate prepared according to the process of the invention preferably has the characteristics of the stable monoclinic form of asenapine maleate of the present invention.

Within the scope of the present invention the carrier gas used in the micronisation process may, for example, be air, dehumidified air, dry oil-free air, noble gases, nitrogen or mixtures thereof. Air is preferred, most preferably dry oil-free air.

A preferred screening wheel speed in the micronisation process may be equal to or below 200 revolutions per minute.

The gas jet mills that are preferably used in the process of the present invention are characterised in that the particles to be micronized are comminuted in a fluidised bed of powder. This bed of powder forming within the micronisation chamber is also referred to in the prior art as a fluidised bed, or fluid bed.

The monoclinic crystals of asenapine maleate, which are subjected to the micronisation process of the invention, may be prepared by crystallization of asenapine maleate according to a process similar to that disclosed in example 1 of EP 1 710 245 B1 and EP 1 917 267 B1. This crystallization process of asenapine maleate comprises, in general terms, the cooling of an ethanol solution containing asenapine maleate, and optionally the seeding thereof with asenapine maleate monoclinic crystals, followed by collection of the obtained crystals. The crystallization processes disclosed according to the present invention lead to asenapine maleate monoclinic crystals of greater polymorphic purity than that prepared in the above prior art. The asenapine maleate monoclinic crystals so produced may contain a percentage of orthorhombic form significantly less than 1% by weight. The crystallisation processes of the present invention also typically lead to crystals having a lower d90 value than in the above prior art. The polymorphically pure form of monoclinic asenapine maleate produced by the crystallisation processes of the present invention also shows high polymorphic stability, for example following micronisation. For example, a number of samples obtained by the crystallisation processes, and having a particle size d90 of 40 microns or less, were stored for 1 month under ambient conditions (atmospheric pressure and 15° C.-28° C.), and were found to be stable. As used herein, the term "collection" comprises filtration, washing and drying steps.

The particle size distribution of the input monoclinic crystals of asenapine maleate which are subjected to the micronisation process of the invention, is fundament ally of secondary importance to the feasibility of the process according to the invention. Usually, monoclinic crystals of asenapine maleate which have a particle size distribution characterized by a d90 from 1000 μm to 20 μm or less, from 1000 μm to 40 μm or less, from 500 μm to 40 μm or less, or from 200 μm to 40 μm or less, for example, are used in the process according to the invention. In addition, the input monoclinic crystals of asenapine maleate which are subjected to the aforementioned micronisation process, are characterised by having a high polymorphic purity, preferably more than 95% by weight of the monoclinic form, more preferably more than 98% by weight of the monoclinic form, most preferably more than 99% by weight of the monoclinic form of asenapine maleate.

The present invention also provides a stable, micronised monoclinic form of asenapine maleate, which is obtained or obtainable by the micronisation process of the present invention.

In another aspect, the present invention provides a process for obtaining asenapine maleate monoclinic form of high polymorphic purity, the process comprising i) dissolving asenapine maleate in ethanol, optionally in the presence of a surfactant, and refluxing the solution of asenapine maleate obtained, ii) cooling the solution to 10° C.-30° C. under conditions of forced or controlled cooling, iii) optionally seeding the solution with asenapine maleate monoclinic crystals and/or optionally adding a surfactant, iv) optionally cooling the mixture from the temperature reached in step (ii) to −10° C. to 10° C. (such as −5° C. to 5° C., for example 0° C. to 5° C.) under conditions of forced or controlled cooling, and v) collecting the crystals so obtained. The invention also provides monoclinic asenapine maleate obtained or obtainable by this process.

The preferred temperature range to which the mixture is cooled in step (iv) may be 0° C. to 5° C.

The optional seeding with monoclinic crystals and/or the optional addition of surfactant of step (iii) may take place during the cooling of step (ii). Thus, step (ii) may be split into two or more stages, such that these optional materials may be added at the end of a given cooling stage, with further cooling of step (ii) taking place thereafter.

In particular embodiments, the process of this aspect comprises dissolving asenapine maleate in ethanol, refluxing the solution of asenapine maleate obtained, cooling the solution to 15° C.-30° C. under conditions of forced cooling, optionally seeding the solution with asenapine maleate monoclinic crystals, followed by collection of the crystals so obtained.

In accordance with such embodiments, the solution is preferably cooled to around 30° C., preferably over a period of around 15 minutes. The cooling rate during the step of forced cooling is preferably around 2° C.-4° C. (e.g. 3° C.-4° C.) per minute. The term 'forced cooling' means that the solution of asenapine maleate is subjected to conditions which cause its temperature to fall at a faster rate than would occur under ambient conditions following removal of the heat source used for the refluxing step. For example, a cooling jacket may be used, involving the circulation of cold water around the vessel containing the solution. In a preferred embodiment, the refluxing step takes place for around 15 minutes.

The cooling during step (iv) may take place at a rate of between 0.5° C. to 2° C. per minute, for example at around 1° C. per minute.

The monoclinic asenapine maleate obtained according to the crystallisation process of the invention has a higher polymorphic purity than that obtained by processes of the prior art, containing a percentage of orthorhombic form significantly less than 1% by weight. The process also tends to result in a lower particle size of the obtained crystals, having a d90 value preferably equal to or below 45 μm, more preferably between 45 μm and 32 μm. Said polymorphically pure form of monoclinic asenapine maleate also shows high polymorphic stability, for example to micronisation.

In particular embodiments, the crystallisation process of the present invention comprises crystallization of asenapine maleate in the presence of one or more surfactants. The surfactant used in this process may be added before or after the generation of the monoclinic crystals of asenapine maleate (i.e. in step (i) or step (ii), respectively). In a preferred embodiment, the surfactant is added before the generation of the monoclinic crystals of asenapine maleate (i.e. in step (i)). The crystallization of asenapine maleate according to this process preferably comprises: dissolving a mixture of asenapine maleate and a surfactant in ethanol at reflux temperature; followed by cooling the solution obtained to around 0° C. (e.g. from −10° C. to 10° C., such as −5° C. to 5° C., more preferably −5° C. to 0° C. or 0° C. to 5° C.) under conditions of controlled cooling; optionally seeding the solution with asenapine maleate monoclinic crystals; and finally collecting the crystals so obtained. When the solution is seeded with asenapine maleate monoclinic crystals, this seeding is preferably carried out when said solution cools to a temperature of approximately 30° C.

The "controlled cooling" used in such embodiments means that the solution of asenapine maleate and surfactant is subjected to conditions which cause the refluxing temperature of the ethanol to fall at a controlled rate. The controlled rate may, for example, be from 1° C. to 5° C. per minute, for example about 3° C. per minute, until a temperature around 10° C. is reached; followed by a second controlled rate of around 0.5° C. to 2° C. per minute, for example around 1° C. per minute, until a temperature around 0° C. is reached.

The asenapine maleate monoclinic form of the present invention, prepared according to the said process, exhibits high polymorphic purity and stability over time, and low particle size, The monoclinic crystals of asenapine maleate obtained by the crystallisation process of the invention may also be subjected to the micronisation process of the invention.

As used herein, the term "surfactant" refers to a substance or substances which exhibit some surface or interfacial activity. Suitable surfactants are selected from non-ionic, anionic, cationic, amphoteric surfactants or mixtures thereof. Preferably, the surfactant is a non-ionic surfactant or a mixture thereof. Non-limiting examples of non-ionic surfactants include saturated and/or unsaturated fatty acids having the structural formula CH3 (CH2)m COOH where m is in the range of 6 to 18 (such as stearic acid, lauric acid, capric acid, myristic acid, caprylic acid, oleic acid) and their derivatives fatty alcohols (such as lauryl alcohol, cetyl alcohol, stearyl alcohol, capryl alcohol, cetyl stearyl alcohol, lauryl myristyl alcohol, oleyl alcohol), glyceryl esters including mono-, di- and tri-glycerides (such as glyceryl monostearate, glyceryl monolaurate), fatty acid esters of fatty alcohols and/or fatty acid esters of other alcohols including propylene glycol, polyethylene glycol (PEG), sorbitan, sucrose and cholesterol (such as PEG monolaurate, PEG monostearate, sorbitan monolaurate (sold under the trademark SPAN® 20), sorbitan monopalmitate (sold under the trademark SPAN® 40), sorbitan monooleate (sold under the trademark SPAN® 80), sorbitan monostearate (sold under the trademark SPAN® 60), sorbitan tristearate (sold under the trademark SPAN® 65), sorbitan trioleate (sold under the trademark SPAN® 85)); polyoxyethylene sorbitan fatty acid esters (such as polyoxyethylene 20 sorbitan monooleate (also called polysorbate 80 or sold under the TWEEN® 80), polyoxyethylene 20 sorbitan monostearate (also called polysorbate 60 or sold under the trademark TWEEN® 60), polyoxyethylene 20 sorbitan monopalmitate (also called polysorbate 40 or sold under the trademark TWEEN® 40), polyoxyethylene 20 sorbitan monolaurate (also called polysorbate 20 or sold under the trademark TWEEN® 20); polyoxyethylene glyceryl esters (such as polyoxyethylene glyceryl monostearate, polyoxyethylene glyceryl monooleate); polyoxyethylene castor oil derivatives (such as polyoxyl 40 hydrogenated castor oil (sold under the trademark CREMOPHOR® RH 40), polyoxyl 35 castor oil (sold under the trademark CREMOPHOR® EL), polyoxyl 60 hydrogenated castor oil (sold under the trademark CREMOPHOR® RH 60)); polyoxyethylene steroidal esters; polyoxypropylene glyceryl esters; polyoxypropylene steroidal esters; polyoxyethylene ethers; polyglycol ethers; polyoxyethylene-polyoxypropylene copolymers (also called poloxamers or pluronics).

Preferred surfactants that can be used in the crystallisation process include glyceryl esters including mono-, di- and tri-glycerides (such as glyceryl monostearate, glyceryl monolaurate), polyoxyethylene sorbitan fatty acid esters, polyoxyethylene castor oil derivatives or mixtures thereof. Preferably, the surfactant is glyceryl monostearate, a TWEEN® material, such as TWEEN® 80 (also called polyoxyethylene 20 sorbitan monooleate or polysorbate 80) and TWEEN® 60 (also called polyoxyethylene 20 sorbitan monostearate or polysorbate 60), a CREMOPHOR® material, such as Cremophor RH 40 (also called polyoxyl 40 hydrogenated castor oil) or mixtures thereof.

In a preferred embodiment, the surfactant is added in an amount from 0.1% to 5% by weight relative to the weight of the asenapine maleate, preferably in an amount from 1% to 4% by weight relative to the weight of the asenapine maleate, more preferably from 2% to 3% and most preferably in amount of 2.5% by weight relative to the weight of the asenapine maleate.

The monoclinic asenapine maleate obtained according to the particular embodiments of the crystallisation process of the invention employing surfactant and described above process has a higher polymorphic purity than that obtained by processes of the prior art, containing a percentage of orthorhombic form significantly less than 1% by weight. Such a process tends to result in a lower particle size of the obtained crystals, having a d90 value preferably equal to or below 100 μm, preferably 55 μm or below (e.g. 53 μm or lower), more preferably equal to or below 40 μm (e.g. 37 μm or lower). Said polymorphically pure form of monoclinic asenapine maleate also shows high polymorphic stability, especially to micronisation.

A further aspect of the invention relates to the stable and polymorphically pure form of monoclinic asenapine maleate of low particle size of the invention, in association with one or more pharmaceutically acceptable excipients or additives, in the form of a pharmaceutical composition. Such pharmaceutical composition may take the form of a dosage unit such as a tablet, capsule or a suppository. A preferred pharmaceutical composition is a tablet. Most preferably, the composition is a sublingual tablet.

A dosage unit of the invention, containing asenapine maleate and suitable for the treatment or prevention of mental disorders such as bipolar disorders, psychosis, or schizophrenia, may contain about 0.0005 mg to 500 mg of the stable and polymorphically pure form of monoclinic asenapine maleate of the invention. A preferred dosage unit may contain 1 mg-20 mg of the stable and polymorphically pure form of monoclinic asenapine maleate of the invention.

The pharmaceutical compositions of this invention may be orally administered in any orally acceptable dosage form including, but not limited to, capsules, tablets, powders, granules, and aqueous suspensions and solutions. These dosage forms are prepared according to techniques well-known in the art of pharmaceutical formulation. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavouring and/or colouring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of the present invention may contain, in addition to the asenapine maleate of the invention, one or more additional active pharmaceutical ingredients known to be efficacious in the treatment or prevention of the conditions indicated herein, or in the treatment of co-morbidities of those conditions.

The present invention also provides a stable micronised monoclinic form of asenapine maleate as defined above, or a pharmaceutical composition as defined above, for use in therapy.

Also provided is a stable micronised monoclinic form of asenapine maleate as defined above, or a pharmaceutical composition as defined above, for use in the treatment or prevention of mental disorders such as bipolar disorders, psychosis, or schizophrenia.

In addition, the present invention provides a method of treatment or prevention of a mental disorder, such as bipolar disorders, psychosis, or schizophrenia, the method comprising the administration, to a subject in need of such treatment or prevention, of a stable micronised monoclinic form of asenapine maleate as defined above, or a pharmaceutical composition as defined above.

In another aspect, the invention provides the use of the stable micronised monoclinic form of asenapine maleate of the invention for the preparation of a medicament for the treatment or prevention of mental disorders, such as bipolar disorders, psychosis, or schizophrenia.

The present invention will now be further illustrated by the following, non-limiting examples, with reference to the enclosed FIGURE.

EXAMPLES

General Methods

Powder X-Ray Diffraction (PXRD) patterns were acquired on a D8 Advance Series 2Theta/Theta powder diffraction system using CuKα-radiation in transmission geometry. The system was equipped with a VÅNTEC-1 single photon counting PSD, a Germanium monochromator, a ninety positions auto changer sample stage, fixed divergence slits and radial soller. Programs used: Data collection with DIFFRAC plus XRD Commander V.2.5.1 and evaluation with EVA V.12.0. The samples were prepared and placed in standard sample holders using two foils of polyacetate. Five hours scans in a range from 8° to 20° in 2θ were carried out.

Laser Diffraction Spectrometry (LDS) was used to determine the Particle Size Distribution (PSD). The samples were prepared by mixing 100 mg of asenapine maleate with 5 ml of heptane containing 0.2% of Span-20. Ultrasonic treatment of the samples was performed for 5 minutes and the PSD was analysed using a particle size analyzer Malvern Mastersizer 2000.

Example 1

Recrystallization of Asenapine Maleate Monoclinic Form 46.3 g of asenapine maleate (115 mmol), were refluxed for 15 minutes with 139 ml of absolute ethanol. The sample was cooled to 30° C. in 15 minutes, seeded with asenapine maleate monoclinic polymorph and stirred at 15° C.-20° C. for 2 hours and at 0° C.-5° C. for 2 more hours. The suspension was filtered, washed with 25 ml of cold absolute ethanol and dried for 12 h at 45° C. 41.6 g of asenapine maleate monoclinic polymorph was obtained as a white solid. PXRD of the obtained white solid corresponded to pure monoclinic form, or contained a percentage of orthorhombic form significantly less than 1% by weight (FIG. 1). Particle Size Distributions (PSD) of samples obtained by this process were as described in Examples 2-5 below.

Example 2 (Comparative Example)

Preparation of Asenapine Maleate Monoclinic Form having a PSD Characterized by a d90 of 5.7 μm Pure monoclinic form of asenapine maleate having a PSD characterised by a d90 of 32 μm (d95 of 42 μm), obtained as described in Example 1, was micronised at room temperature (20° C.-25° C.) in a Micro-Macinazione Minimicro MC50 stainless steel Jet-mill using dry oil-free air as the carrier gas and a micronisation pressure of 6 bar. The micronised monoclinic asenapine maleate had a particle size, d90, of 5.7 μm and a d95 of 6.6 μm and contained about 5% by weight of the orthorhombic form, as determined by PXRD.

The micronisation process of crystalline asenapine maleate takes place with a partial retention of the product in the microniser. Thus, the amount of samples and the yield depended on the type of microniser and are therefore not key considerations.

Example 3 (Comparative Example)

Preparation of Asenapine Maleate Monoclinic Form having a PSD Characterized by a d90 of 7.7 μm Pure monoclinic form of asenapine maleate having a PSD characterised by a d90 of 32 μm (d95 of 42 μm) and obtained as described in Example 1, was micronised at room temperature (20° C.-25° C.) in a Micro-Macinazione Minimicro MC50 stainless steel Jet-mill by using dry oil-free air as the carrier gas and a micronisation pressure of 3 bar. The micronised product (d90 of 7.7 μm, d95 of 9.1 μm) corresponded to monoclinic form, containing about 3% by weight of the orthorhombic form, as determined by PXRD.

Example 4

Preparation of Asenapine Maleate Monoclinic Form having a PSD Characterized by a d90 of 9.6 μm Pure monoclinic form of asenapine maleate having a PSD characterised by a d90 of 45 μm (d95 of 62 μm) and obtained as described in Example 1, was micronised at a temperature between 6.2° C. and 8.5° C. in a Micro-Macinazione Minimicro MC50 stainless steel Jet-mill by using dry oil-free air as the carrier gas and a micronisation pressure of 3 bar. The obtained micronised product had a d90 of 9.6 μm, d95 of 11.6 μm and showed a high polymorphic purity (>99% by weight monoclinic form), containing less than 1% by weight of the orthorhombic form, as determined by PXRD.

Example 5

Preparation of Asenapine Maleate Monoclinic Form having a PSD Characterized by a d90 of 7.3 μm Pure monoclinic form of asenapine maleate having a PSD characterised by a d90 of 45 μm (d95 of 62 μm) and obtained as described in Example 1, was micronised at a temperature between −30° C. and −40° C. in a Micro-Macinazione Minimicro MC50 stainless steel Jet-mill by using dry oil-free air as the carrier gas and a micronisation pressure of 3 bar. The micronised product (d90 of 7.3 μm, d95 of 8.8 μm) showed a high polymorphic purity (>99% by weight monoclinic form), containing less than 1% by weight of the orthorhombic form, as determined by PXRD.

Example 6

Preparation of Asenapine Maleate Monoclinic Form having a PSD Characterized by a d90 of 9.5 μm Pure monoclinic form of asenapine maleate having a PSD characterised by a d90 of 45 μm (d95 of 62 μm) and obtained as described in Example 1, was micronised at a temperature between 6.2° C. and 8.5° C. in a Micro-Macinazione Mini-micro MC50 stainless steel Jet-mill by using dry oil-free air as the carrier gas and a micronisation pressure of 3 bar. The obtained micronised product had a d90 of 9.5 μm, d95 of 11.6 μm and showed a high polymorphic purity (>99% by weight monoclinic form), containing less than 1% by weight of the orthorhombic form, as determined by PXRD.

Example 7

Preparation of Asenapine Maleate Monoclinic Form by Crystallization in Presence of Cremophor RH40

7.2 g of asenapine maleate (17.9 mmol) and 2.5% (w/w) of Cremophor RH40 were dissolved in 36 mL of absolute ethanol at the reflux temperature of the solvent. The solution obtained was stirred (150 rpm using an overhead U-shape stirrer) at this temperature for 15 minutes, followed by cooling to 10° C. at a cooling rate of 3° C./min. During the cooling process, the solution was seeded with asenapine maleate monoclinic form (0.5% (w/w)) when a temperature of 30° C. was reached. After cooling to 10° C., the solution was further cooled to 0° C. at a cooling rate of 1° C./min, and stirred at this temperature for 1 hour. The suspension obtained was filtered, washed with cold absolute ethanol (5 mL) and dried under vacuum (2 mbar) at 45° C. for 4 hours. 6.12 g (yield: 85%) of a solid, with a PXRD pattern that corresponds to monoclinic form was obtained. PSD is characterized by a d90 of 46 μm and a d95 of 56 μm.

Example 8

Preparation of Asenapine Maleate Monoclinic Form by Crystallization in Presence of Tween 80

14.4 g of asenapine maleate (35.8 mmol) and 2.5% (w/w) of Tween 80 were dissolved in 36 mL of absolute ethanol at the reflux temperature of the solvent. The solution obtained was stirred (150 rpm using an overhead U-shape stirrer) at this temperature for 15 minutes, followed by cooling to 10° C. at a cooling rate of 3° C./min. During the cooling process, the solution is seeded with asenapine maleate monoclinic form (0.5% (w/w)) when a temperature of 30° C. was reached. After cooling to 10° C., the solution was further cooled to 0° C. at a cooling rate of 1° C./min, and stirred at this temperature for 1 hour. The suspension obtained was filtered, washed with cold absolute ethanol (5 mL) and dried under vacuum (2 mbar) at 45° C. for 4 hours. 12.96 g (yield: 90%) of a solid, with a PXRD pattern that corresponds to monoclinic form was obtained. PSD is characterized by a d90 of 37 μm and a d95 of 49 μm.

Example 9

Preparation of Asenapine Maleate Monoclinic Form by Crystallization in Presence of Glyceryl Monostearate 7.2 g of asenapine maleate (17.9 mmol) and 2.5% (w/w) of glyceryl monostearate were dissolved in 36 mL of absolute ethanol at the reflux temperature of the solvent. The solution obtained was stirred (150 rpm using an overhead U-shape stirrer) at this temperature for 15 minutes, followed by cooling to 10° C. at a cooling rate of 3° C./min. During the cooling process, the solution is seeded with asenapine maleate monoclinic form (0.5% (w/w)) when a temperature of 30° C. was reached. After cooling to 10° C., the solution was further cooled to 0° C. at a cooling rate of 1° C./min, and stirred at this temperature for 1 hour. The suspension obtained was filtered, washed with cold absolute ethanol (5 mL) and dried under vacuum (2 mbar) at 45° C. for 4 hours. 6.26 g (yield: 87%) of a solid, with a PXRD pattern that corresponds to monoclinic form was obtained. PSD is characterized by a d90 of 53 μm.

Stability Assays of the Micronised Samples

Stability assays of the new stable monoclinic form of asenapine maleate obtained as described above were performed after 1 month, 2 months and 3 months. The samples were placed into two different types of containers, transparent and opaque vacuum containers. The stability tests were carried out at two different storage conditions, 25° C. and 60% relative humidity (RH), and at 40° C. and 75% RH. The results are shown in Table 1. The same results were obtained using transparent and opaque vacuum containers. It has also been proved that the asenapine maleate of the invention material remained polymorphically stable, being more than 95% by weight of the monoclinic form, after 6 months and 12 months.

As can be seen from the results, using the process of the invention, a stable form of monoclinic asenapine maleate is obtained. Conversely, when micronisation is carried out at a temperature higher than that required by the process of the invention, the asenapine maleate obtained is not stable, and conversion of the monoclinic to the orthorhombic form occurs to a significant extent.

TABLE 1

Stability assays of micronised samples

| | Particle size before micron-isation d90 (μm) | Pressure (bar) | Temperature of micronisation (° C.) | Particle size after micron-isation d90 (μm) | % of orthorhombic form in the micronised product | Stability test conditions | | | | | | |
|---|---|---|---|---|---|---|---|---|---|---|---|---|
| | | | | | | 25° C.-60% RH % of orthorhombic form | | | | 40° C.-75% RH % of orthorhombic form | | |
| Example | | | | | | after 1 month | after 2 months | after 3 months | after 6 months | after 1 month | after 2 months | after 3 months |
| 2 | 32 | 6 | 20-25 | 5.7 | 5% | — | — | — | — | 9% | — | 13% |
| 3 | 32 | 3 | 20-25 | 7.7 | 3% | — | — | — | — | 5% | — | 8% |
| 4 | 45 | 3 | 6.2-8.5 | 9.6 | <1% | Not detected | Not detected | Not detected | Not detected | Not detected | Not detected | Not detected |

TABLE 1-continued

Stability assays of micronised samples

| Example | Particle size before micron- isation d90 (μm) | Pressure (bar) | Temperature of micronisation (°C.) | Particle size after micron- isation d90 (μm) | % of orthorhombic form in the micronised product | 25° C.-60% RH % of orthorhombic form | | | | 40° C.-75% RH % of orthorhombic form | | |
|---|---|---|---|---|---|---|---|---|---|---|---|---|
| | | | | | | after 1 month | after 2 months | after 3 months | after 6 months | after 1 months | after 2 months | after 3 months |
| 5 | 45 | 3 | −30/−40 | 7.3 | <1% | Not detected | Not detected | Not detected | Not detected | Not detected | Not detected | Not detected |
| 2.1 | 32 | 6 | 20-25 | 5.7 | <1% | 5% | — | — | — | 8% | — | 12% |
| 3.1 | 32 | 3 | 20-25 | 7.7 | <1% | 3% | — | — | — | 4% | — | 7% |

Example 2.1 used the same input material and conditions as Example 2. The lack of long-term polymorphic stability is illustrated.
Example 3.1 used the same input material and conditions as Example 3. The lack of long-term polymorphic stability is illustrated.

The invention claimed is:

1. A process for the preparation of a stable micronised monoclinic form of asenapine maleate which comprises 5% by weight or less of orthorhombic form or any other crystalline form of asenapine maleate, wherein the asenapine maleate has a particle size distribution characterised by a d90 equal to or below 40 μm, and which remains polymorphically stable after 3 months of storage, the process comprising the micronisation of monoclinic asenapine maleate wherein the applied micronisation pressure is below 7 bar and the micronisation temperature is 10° C. or below.

2. The process according to claim 1, wherein the applied micronisation pressure is 5 bar or below and the micronisation temperature is −10° C. or below.

3. The process according to claim 1, wherein the applied micronisation pressure is 3 bar or below and the micronisation temperature is −10° C. or below.

4. The process according to claim 1, wherein the monoclinic asenapine maleate used for micronisation is obtained by a process comprising dissolving a mixture of asenapine maleate and a surfactant in ethanol at reflux temperature; followed by cooling the solution obtained to 0° C. under conditions of controlled cooling; optionally seeding the solution with asenapine maleate monoclinic crystals; and finally collecting the crystals so obtained.

5. The process according to claim 1, wherein the monoclinic asenapine maleate used for micronisation is obtained by a process comprising dissolving asenapine maleate in ethanol, refluxing the solution of asenapine maleate obtained, cooling the solution to 15-30° C. under conditions of forced cooling, optionally seeding the solution with asenapine maleate monoclinic crystals, followed by collection of the crystals so obtained.

6. The process according to claim 1, wherein the applied micronisation pressure is 3 bar or below and the micronisation temperature is 10° C. or below.

7. The process according to claim 1, wherein the stable micronised form of asenapine maleate comprises 2% by weight or less of orthorhombic form or any other crystalline form of asenapine maleate.

8. The process according to claim 1 or claim 7, wherein the stable micronised form of asenapine maleate has a particle size distribution characterised by a d90 of 30 μm or below.

9. The process according to claim 8, wherein the stable micronised form of asenapine maleate has a particle size distribution characterised by a d90 of 10 μm or below.

10. The process according to claim 1, wherein the stable micronised form of asenapine maleate comprises 1% by weight or less of any other crystalline form of asenapine maleate.

* * * * *